United States Patent [19]
Ohshima et al.

[11] 3,947,518
[45] Mar. 30, 1976

[54] PROCESS FOR PURIFYING ACRYLAMIDES
[75] Inventors: Iwao Ohshima; Seiichi Chiba; Kenzo Ariyama, all of Yokohama; Yasuo Ogawa, Kawasaki; Masahide Ozaki, Yokohama, all of Japan
[73] Assignee: Nitto Kagaku Kogyo Kabushiki Kaisha, Japan
[22] Filed: Apr. 29, 1974
[21] Appl. No.: 465,303

[30] Foreign Application Priority Data
May 2, 1973   Japan.............................. 48-49506

[52] U.S. Cl......................... 260/561 N; 260/561 R
[51] Int. Cl.²...................................... C07C 103/08
[58] Field of Search..................... 260/561 R, 561 N

[56] References Cited
UNITED STATES PATENTS
3,023,242   2/1962   Bornemann et al............ 260/561 N
3,527,803   9/1970   Bruschtein..................... 260/561 N FOREIGN PATENTS OR APPLICATIONS
996,692   6/1965   United Kingdom............ 260/561 N

OTHER PUBLICATIONS

Chem. Abs., 60, 4014h (1964) — (Abstract of Japanese Pat. 13,360/63).

Chem. Abs., 79, 67046 (1973) — (Abstract of Ger. Offen. 2,259,796).

*Primary Examiner*—C. Davis
*Attorney, Agent, or Firm*—Robert E. Burns; Emmanuel J. Lobato; Bruce L. Adams

[57] ABSTRACT

Process for purifying an acrylamide including the steps of (1) adding an inorganic base (excluding ammonia) to an aqueous solution containing 15 to 60% by weight of the acrylamide at a temperature of up to 60°C in an amount of 0.1 to 1.5 wt. % based on the acrylamide and (2) blowing a gas, inert to the acrylamide, into the resulting mixture at a hydrogen ion concentration of a pH of 12 to 13.7 and if necessary, (3) subjecting the so treated acrylamide solution to an active carbon adsorption treatment.

15 Claims, No Drawings

PROCESS FOR PURIFYING ACRYLAMIDES

BACKGROUND OF THE INVENTION

Technical Field

The present invention relates to a process for purifying acrylamides. More particularly, it is concerned with a process by which a highly concentrated aqueous solution of high molecular weight polymers containing substantially no cross linkage can be obtained by removing any trace of bifunctional cross linking impurities from acrylamide.

Background

Recently, water-soluble acrylamide polymers have been produced on an industrial scale and widely used as soil stabilizing agents, dry and wet strength enhancing agents for paper, precipitating agents for use in clearing waste water from various industries, and coagulating agents for settling mineral ores or pulp-dispersing agents in the paper making industry and supporting materials for pigments and the like.

For soil stabilizing agent application, water-soluble acrylamide polymers are used in the form a gel in which cross linking monomers are positively added thereto, while for the dry and wet strength enhancing agents for paper, the polymer used has a relatively low molecular weight in the order of several hundred thousands, and in both cases, the trace of bifunctional cross linking impurities contained in commercial acrylamides can be neglected.

On the other hand, the utilization of acrylamide polymers as a coagulating agent has rapidly increased in various fields such as treatment of waste water from various industries as well as homes and clarification of rivers in order to prevent pollution of the environment. It is said that the coagulating capability of an acrylamide polymer is almost proportional to its molecular weight. Therefore, acrylamide polymers are required to have higher molecular weights, e.g., molecular weights above several million and, recently, acrylamide polymers having molecular weights above ten million have been used. In the production of a coagulating agent which is required to have such a remarkably high molecular weight, a trace of bifunctional cross linking impurities contained in a commercial acrylamide affects the water solubility of the polyacrylamide to an appreciable extent.

As can be seen in Table 1, the water solubility of polyacrylamide produced from the commerical acrylamide is little influenced by bifunctional cross linking impurities (hereinafter referred to merely as impurities) at a relatively low concentration of the acrylamide, i.e., up to 10% by weight. However, when the acrylamide concentration in a polymerization system exceeds 10% by weight, the influence of such impurities gradually appears. With a concentration of 20% by weight, the commercial acrylamide is greatly influenced by the impurities, and an acrylamide which should be water-soluble in nature may become water insolubilized.

Table 1

| Aqueous solution of acrylamide alone Polymerization redox system catalyst | | | | | | |
|---|---|---|---|---|---|---|
| | Water solubility | | | | | |
| Concentration of system Commercial acrylamide | 5% | 10% | 15% | 20% | 25% | 30% |
| A | O | O | Δ | X | X | XX |
| B | O | Δ | X | X | XX | XX |
| C | O | Δ | X | X | XX | XX |
| D | O | O | Δ | X | X | XX |

O — uniformly dissolved
Δ — a trace of insoluble matter
X — a large quantity of insoluble matter
XX — remarkably insoluble In general, a recrystallization method is known to remove the impurities, i.e., to purify an acrylamide. In fact, when the commercial acrylamides of respective companies are purified by recrystallization, the polymers obtained are all water-soluble, which indicates that the formation of insoluble matter is attributable to the presence of the impurities. However, such a recrystallization method entails high cost. Further, when such materials as acrylamides which easily tend to polymerize are recrystallized, many difficulties due to polymerization phenomena arise and hinder normal operation.

Although the present invention does not intend to analyze these impurities accurately, it may be easily expected that the impurities are any of compounds having a certain type of divinyl structure. It is known that acrylamide produces diacrylimide with the formation of imide under acid conditions. Therefore, it may be easily estimated that the diacrylimide will be produced in the course of the production of acrylamide.

Since such an impurity as a diacrylimide may be easily hydrolyzed with an alkali, an alkali treatment of crude acrylamide may be a useful method for removing the diacrylimide. Such a purifying method is far more simple to carry out than a recrystallization method and has been expected to be put into industrial practice.

However, the alkali treatment of the crude acrylamide necessarily induces hydrolysis of the acrylamide at the same time even if an impurity which is easy to hydrolyze is hydrolyzed. Because of the formation of acrylic acid by the hydrolysis of acrylamide and the loss of acrylamide by any other reactions, it is not logical to make an acrylamide solution alkaline. In fact, Japanese Pat. No. 11612/64 discloses that an acrylamide is reduced by one half at a pH of 11.6 (a 1N aqueous ammonia solution) in about five hours, and it is almost entirely lost at a pH of 13.6 (a 1N aqueous sodium hydroxide solution) in about 6 hours.

Now, the applicants having discovered as a result of their studies that the loss of an acrylamide under a basic condition is due to the ammonia generated by the decomposition of the ammonium salts (which are produced during ammonia neutralization of acrylamide sulfates) contained in the acrylamide and the hydrolysis of the acrylamide (i.e. the formation of acrylic acid and ammonia). That is, the ammonia generated by these causes reacts with three molecules of the acrylamide to form 3,3',3''-nitrilotripropinamide (hereinafter referred to as NPA). That is, 1 mole (17g) of ammonia is generated at the expense of 3 moles (213g) of acrylamide. However, the NPA is known to be a chain transfer agent and a reducing component of redox type initiators. Therefore, the presence of this material is very unfavourable in the production of high molecular weight acrylamide polymers suitable for a coagulating agent by a polymerization process.

SUMMARY OF THE INVENTION

It is an object of the present invention to alkali-hydrolyze the easily hydrolyzable impurities present in a crude acrylamide by treating the acrylamide with an alkali, thereby rendering the impurities harmless.

The present invention contemplates the attainment of this object by treating the crude acrylamide with an alkali under particular conditions and removing the ammonia evolved together with a gas which is blown into the system.

Therefore, the process for purifying an acrylamide in accordance with the present invention is characterized in that an inorganic base (excluding ammonia) is added to an aqueous solution containing 15 to 60% by weight of the acrylamide at a temperature up to 60°C in a quantity of 0.1 to 1.5% based on the acrylamide, and a gas inert to the acrylamide is blown into the resulting mixture at a hydrogen ion concentration of a pH of 12 to 13.7.

In this manner, the present invention has succeeded in realizing the contradictory effects of promoting the hydrolysis of the easily hydrolyzable impurities under alkaline conditions while suppressing the hydrolysis of the acrylamide to control the formation of NPA. That is, when air is blown into an aqueous solution containing 15 to 60% by weight of an acrylamide and having a pH of 12 to 13.7 at a temperature of up to 60°C to drive off the ammonia generated from within the system, little loss of the acrylamide due to the formation of NPA is observed.

More surprisingly, even with a 50% aqueous acrylamide solution under extremely severe conditions such as its pH value adjusted to 13.5 with the addition of 1% sodium hydroxide (with respect to the acrylamide) and its temperature maintained at 50°C, acrylic acid is produced in a negligibly small quantity (see, Comparative Examples 1 and 2 set forth hereinafter). The gas blown in may be air, and pH control may be carried out by means of sodium hydroxide which is inexpensive and easy to handle.

Therefore, the purifying process according to the present invention can be utilized for any acrylamide product on the market at any place by an acrylamide user, e.g., a manufacturer of an acrylamide polymer coagulating agent. Further, avoiding the inclusion of an indefinite amount of ammonia (which acts as a reducing agent) is effective for stabilization of the polymerizable property of acrylamide.

In the purifying process according to the present invention, the behavior of the easily hydrolyzable impurities is determined by neutralizing the aqueous acrylamide solution after the purifying treatment, polymerizing the resulting solution through the use of a conventional polymerization initiator, and observing the dissolving state of the resulting polymer to examine for the presence of the undissolved matter because there is no standard analytical procedure therefor. Surprisingly, the result indicates that most of the commercial acrylamides shown in Table 1 provide aqueous solutions containing no undissolved matter whatsoever. This fact indicates that the easily hydrolyzable impurities may be rendered harmless by the purifying process of the present invention and at the same time, that most of the impurities contained in the commercial acrylamides are easily hydrolyzable impurities.

In addition, although very unusual, there are present certain types of acrylamides which still leave undissolved substances even after they have been subjected to the purification of the present invention. In this case, it is considered that these acrylamides contain other impurities which are difficult to hydrolyze. For the purification of such acrylamides, difficult to hydrolyze, they may be subjected to adsorption treatment with active carbon after (or simultaneously with or before) carrying out the purifying process of the present invention. One of the impurities which are difficult to hydrolyze is considered to be methylenebisacrylamide. An acrylamide to which methylenebisacrylamide has been added and a commercial acrylamide containing impurities which are difficult to hydrolyze exhibit an entirely similar behavior when they are subjected to an active carbon treatment.

DETAILED DESCRIPTION OF THE INVENTION

1. Acrylamide

The term "acrylamide" as used herein denotes, in addition to a non-substituted acrylamide ($CH_2 = CHCONH_2$), an $\alpha$- or $\beta$- or N-substituted acrylamide having a water solubility sufficient to provide an aqueous solution with the desired concentrations which is used singly or as a mixture thereof or with a small amount of other water-soluble monomers. Illustrative examples of these acrylamide derivatives include methacrylamide, N-methylolacrylamide and N-methylolmethacrylamide. Illustrative examples of the monomer mixture are a mixture of acrylamide and methacrylamide, a mixture of acrylamide and methylolacrylamide, a mixture of a predominant quantity (above 50% by weight) of these acrylamides or derivatives thereof and other monomers, preferably water-soluble, such as acrylic acid or acrylates, methacrylic acid and methacrylates, hydroxy alkyl (e.g., ethyl and propyl) esters of acrylic and methacrylic acid, acrylonitrile, methacrylonitrile, and lower alkyl ($C_4$ or less) esters of acrylic acid.

The aqueous solution of the acrylamide with which the present invention is concerned may be prepared from a commerical crystalline acrylamide or acrylamide solution, Also it may be an aqueous solution obtained in the production of an acrylamide. For example, an aqueous acrylamide solution obtained by direct hydration of acrylonitrile (in which, preferably, catalysts are removed or acrylamide sulfates are neutralized with ammonia, ammonium carbonate, caustic alkalis, calcium carbonate and the like, and more preferably, the sulfate byproducts are removed) is typical.

2. Purification

Aqueous acrylamide solution

An aqueous acrylamide solution suitable for use in the purifying process of the present invention has a concentration of 15 to 60% by weight. The solvents used in the present invention may be, in addition to water, an aqueous solution of water-soluble organic solvents such as lower alcohols, polyol, lower ketones, lower ethers and the like.

Inorganic base

Any water-soluble inorganic base excluding ammonia may be used. The term "base" as used herein denotes all compounds capable of bringing the pH of an aqueous acrylamide solution into a range of 12 to 13.7. Also, the term "water-soluble" as used herein denotes a water-solubility of such a degree that the inorganic bases can provide such pH values.

Illustrative examples of the water-soluble inorganic base include hydroxides, oxides and weak acid salts such as carbonates or phosphates of alkali metals and alkaline earth metals. Among these materials, sodium hydroxide and potassium hydroxide are preferred because they provide no precipitation of salts after neutralization.

A buffer agent may be used to maintain a pH value within the range of from 12 to 13.7.

Inert gas

The gas used in the purifying process of the present invention should be inert to acrylamide. Since the purifying system is alkaline, the gas used is, desirably, not acid. Further, it is desirable that the gas used not be water-soluble.

Illustrative examples of a gas suitable for use in the purifying process of the present invention include air, nitrogen, argon, carbon monoxide, oxygen, hydrogen, nitrogen oxides, lower hydrocarbons, and mixtures thereof.

Among these gases, air is the most preferred because air prevents acrylamide from polymerizing during a purifying treatment by the oxygen contained in air. In addition to air, oxygen or a mixture of oxygen and nitrogen and nitrogen oxides capable of inhibiting polymerization per se may be preferably used singly or in admixture with nitrogen, argon and the like. Further, if there is present any polymerization inhibitor capable of inhibiting the polymerization of an aqueous acrylamide solution at a pH value of 12 to 13.7, it is possible to blow nitrogen, argon and the like into the aqueous acrylamide solution to which such an inhibitor is added. In this case, care should be taken with respect to the residue of the polymerization inhibitor.

Purifying treatment

In the purifying process, the gas as stated above is blown into an aqueous acrylamide solution having a hydrogen ion concentration of a pH value of 12 to 13.7, preferably 12.8 to 13.5 at a temperature up to 60°C, preferably to 40 to 50°C.

In order to bring the pH of an aqueous solution containing 15 to 60% by weight of the acrylamide into a range from 12 to 13.7, caustic alkalis may be added in a quantity of 0.1% by weight or more, preferably 0.2 to 1% by weight based on the acrylamide. To prevent the aqueous acrylamide solution from locally reaching a higher pH value, the inorganic base may be preferably added in the form of an aqueous solution.

The blowing of the gas is preferably started before the addition of the base. In order to remove ammonia effectively, the gas is preferably blown in a manner such that the quantity of bubbles formed is kept at a minimum. For this purpose, in the case where a nozzle having a blowing orifice less than 0.1 mm in diameter is used (specifically speaking, a gas diffuser made of sintered glass or a sintered metal) the gas is blown at a superficial velocity in a column of no less than 0.5 mm/second, preferably 2 to 5 mm/second. In the case where a nozzle having a blowing orifice greater than 0.1 mm in diameter (for example, 2 to 4 mm) is used, the gas is blown at a superficial velocity in a column of no less than 3 mm/second, preferably 7 to 20 mm/second.

The container into which the aqueous acrylamide solution is placed should be of a configuration such that a column of the aqueous acrylamide solution will exist to a certain extent over the gas blowing orifice. So long as a union or channelling of the bubbles of the blown gas is not caused, stirring of the aqueous acrylamide solution, introducing of a solid filler possessing a high surface area (e.g. Rings and saddles) into the solution, operation under reduced pressures, and removal of ammonia accompanied by the blowing gas may be accelerated with the aid of any convenient means.

The time required for the purifying treatment depends upon the amount of the impurities contained in the monomer. 10 minutes to 8 hours, ordinarily 1 to 6 hours, satisfactory. After the purifying treatment, the solution is neutralized, if desired. That is, when the aqueous acrylamide solution after the purification is subjected to copolymerization with anionic monomers or hydrolytic polymerization, neutralization is unnecessary. On the other hand, if a nonionic acrylamide polymer is to be produced, the purified aqueous acrylamide solution may be subjected to a polymerization process after it has been neutralized.

Activated-carbon treatment

For conventional commercial acrylamides, the undissolved impurities after polymerization may be substantially reduced to zero. However, in some cases, the impurities which are difficult to hydrolyze are still remaining, and the undissolved substance may not be reduced to zero. Alternatively, in the case where an acrylamide polymer having a super high molecular weight above 10,000,000 is to be produced, undissolved substances will often remain. In such cases, the remaining impurities may be removed by treating the aqueous acrylamide solution with activated carbon in quantities of not less than 0.5% by weight based on the solution after or simultaneously with or before the hydrolysis of the impurities which are easy to hydrolyze according to the afore-mentioned method. By such a combination with the active carbon treatment, the commercial acrylamides all may be polymerized into acrylamide polymers having a super high molecular weight and containing no undissolved substances.

The active carbon used in the present invention may be any form of active carbon. However, a coconut shell activated carbon produced by a steam process is especially useful. The active carbon treatment may be carried out by an adsorption tower method, a stirring and mixing method, or any other process which affords a solid-liquid contact. The active carbon treatment is preferably carried out also with the blowing of a polymerization inhibiting gas such as air.

EXPERIMENTAL EXAMPLE

Reference Example — 1

A commercial acrylamide was subjected to hydrolyzing treatment under various conditions in which the concentration of the aqueous acrylamide solution the amount (or pH) of sodium hydroxide added, the temperature and the presence and absence of aeration were varied. After the hydrolyzing treatment, the amount of acrylic acid produced and the amount of double bond lost were determined. The hydrolyzed product was further treated for another period of 180 minutes, and neutralized with sulfuric acid to a pH value of 6.0 ± 0.1 and ready for polymerization. The resulting acrylamide solution was taken in an amount such that it contained 160 g of acrylamide monomer and ion-exchanged water was added thereto to make 1,000 g. The resulting solution containing 18% by weight of the monomer was polymerized with the aid of redox initiators at a temperature of 30°C. The resultant gel-like polymer was dissolved in deionated water to a diluted aqueous solution containing 1.0% of the polymer (polyacrylamide). The aqueous solution so produced was examined for the presence and absence of undissolved matters and its viscosity was determined at 25°C by means of a Brookfield viscometer. The results are shown in Table 2.

6,000,000. Every two samples from A, B and C companies were experimented. The result was that all the copolymers produced were dissolved.

However, in the case where the above-mentioned treatment was not conducted, every samples gave a large amount of undissolved matters.

EXAMPLE 2

Table 2

| Condition | Treatment condition | | | | Amount of acrylic acid produced | | | Loss of double bond (calculated in terms of acrylamide) | Polymer properties | |
|---|---|---|---|---|---|---|---|---|---|---|
| Acrylamide | Concentration of acrylamide % (by weight) | Alkali amount and pH (4) | Temperature | Air blowing | 30 minute | 60 minute | 180 minute | | 1.0% viscosity | Undissolved matter |
| (1) No ammonium salt | 20 | 0.20 (12) | 40°C | (3) none | 0.089% | 0.090% | 0.095% | 0.3% | 1,430cp | none |
| | 40 | 0.30 (13) | 25 | (3) none | 0.10 | 0.10 | 0.15 | 0.1 | 1,680 | none |
| | 40 | 0.30 (13) | 40 | conducted | 0.095 | 0.11 | 0.17 | 0.1 | 1,770 | none |
| | 50 | 0.50 (13.4) | 50 | (3) none | 0.18 | 0.24 | 0.33 | 5.9 | 800 | none |
| | 50 | 0.50 (13.4) | 50 | conducted | 0.15 | 0.20 | 0.29 | 0.1 | 1,850 | none |
| (2) 0.31% ammonium calculated in terms of ammonium sulfate | 40 | 0.25 (12.8) | 25 | (3) none | 0.11 | 0.11 | 0.17 | 2.3 | 950 | none |
| | 40 | 0.25 (12.7) | 40 | conducted | 0.14 | 0.16 | 0.19 | 0.1 | 1,610 | none |
| | 50 | 0.50 (13.4) | 50 | (3) none | 0.22 | 0.30 | 0.34 | 14.3 | 130 | none |
| | 50 | 0.50 (13.4) | 50 | conducted | 0.21 | 0.31 | 0.34 | 0.2 | 1,500 | none |

(1) Acrylic acid content 0.086%
(2) Acrylic acid content 0.092%
(3) Treated under a tight seal
(4) Weight percent with respect to monomer

EXAMPLE 1

A 10% by weight aqueous solution of sodium hydroxide (0.5% NaOH with respect to acrylamide) was added to a 40% by weight aqueous acrylamide solution prepared using a commercial acrylamide. The resulting solution had a pH of 13.0. This solution was then heated to a temperature of 40°C and kept at that temperature under air blowing for 60 minutes.

To 50 parts of the acrylamide solution thus treated was added 5 parts of acrylic acid to adjust the pH to 7.0 and to the resulting mixture was added on ion exchanged water to make 100 parts. The resulting solution was adjusted to 30°C and polymerized with the aid of redox initiators to produce an acrylamide-sodium acrylate copolymer having a molecular weight of about Three kinds of acrylamide from B company other than that used in Example 1 were used as a sample and the easily hydrolyzable impurities contained therein were hydrolyzed by the air blowing under various conditions. The hydrolyzed aqueous solution containing 24% of acrylamide alone was polymerized with the aid of redox initiators to produce polyacrylamide having a molecular weight of about 8,000,000.

The solubility and acrylic acid byproduct (after polymerization) of the polyacrylamides are shown in Table 3. It is apparent from Table 3 that all the polyacrylamides were dissolved at a pH of no less than 12 and the acrylic acid was very small.

Table 3

| Acrylamide | Concentration (%) | NaOH Amount (%) | pH | Temperature (°C) | Time (hour) | Undissolved matter | Acrylic acid content in polymer |
|---|---|---|---|---|---|---|---|
| B - 1 | 20 | 0.1 | 13 | 30 | 3 | Absolutely none | 0.72 |
| | 40 | 0.05 | 10 | 30 | 3 | somewhat | 0.48 |
| | 40 | 0.3 | 12 | 50 | 1 | absolutely none | 0.65 |
| | 50 | 0.5 | 13 | 40 | 1 | absolutely none | 0.94 |
| | 50 | 1.0 | 13.5 | 30 | 0.5 | absolutely none | 1.02 |
| B - 2 | 20 | 0.5 | 13.5 | 50 | 0.5 | absolutely none | 0.74 |
| | 20 | 0.2 | 12.6 | 40 | 2 | absolutely none | 0.55 |
| | 50 | 0.04 | 9 | 50 | 3 | somewhat | 0.33 |
| | 50 | 0.5 | 13 | 30 | 3 | absolutely none | 0.87 |
| B - 3 | 20 | 0.07 | 11 | 50 | 6 | somewhat | 0.61 |
| | 40 | 0.2 | 12.9 | 30 | 3 | absolutely none | 0.44 |
| | 50 | 0.7 | 13.3 | 40 | 1 | absolutely none | 0.78 |
| Recrystallized product | — | — | — | — | — | absolutely none | 0.47 |
| Non-refined product | — | — | — | — | — | remarkably | — |

EXAMPLE 3

An acrylamide (X) whose undissolved matters do not disappear as yet even if its easily hydrolyzable impurities were hydrolyzed and an acrylamide (Y) containing 5 ppm of methylenebisacrylamide added thereto, whose undissolved matters having being disappeared by the hydrolysis of its easily hydrolyzable impurities, were subjected to an adsorption treatment by active carbon, respectively.

After the active carbon treatment, the aqueous solution containing 23% of acrylamide was polymerized with the use of a redox initiator to produce polyacrylamide having a molecular weight of about 8,000,000. As indicated in Table 4, no undissolved matters were present.

Table 4

| Acrylamide | Hydrolysis treatment | | | | | Addition of methylenebis-acrylamide | Activated carbon treatment | Undissolved matter |
| --- | --- | --- | --- | --- | --- | --- | --- | --- |
| | concent-ration (%) | NaOH amount (%) | pH | Temper-ature (°C) | Time (hour) | | | |
| X | — | — | — | — | — | — | — | Very large |
| | 50 | 0.25 | 13.4 | 50 | 2 | — | — | somewhat |
| | " | " | " | " | " | — | conducted | absolutely none |
| | — | — | — | — | — | — | — | very large |
| Y | 50 | 0.25 | 13.5 | 50 | 2 | — | — | absolutely none |
| | " | " | " | " | " | 5 ppm | — | remarkable |
| | " | " | " | " | " | " | conducted | absolutely none |

During the hyrolyzation and active carbon treatment, the air blowing was conducted.

EXAMPLE 4

In the production of acrylomide, acrylamide sulfate was neutralized with sodium hydroxide to liberate acrylamide and the byproduced sodium sulfate was separated to provide an aqueous acrylamide solution. To this aqueous acrylamide solution was added sodium hydroxide (0.5% NaOH with respect to acrylamide) to adjust the pH to 13.4 or higher and the resulting solution was kept at a temperature of 50°C under oxygen blowing for an hour. Thereafter, the pH of the solution was adjusted to 6.5 and a coconut shell active carbon was added thereto in an amount of 0.8% relative to the solution. The resultant solution was maintained at a temperature under oxygen blowing for another period of 30 minutes and thereafter, the active carbon was separated.

After the separation of the activated carbon, the acrylamide solution was concentrated to crystallize the acrylamide.

The resulting crystalline acrylamide was polymerized according to the same procedure described in Example 3 to give polyacrylamide. The polyacrylamide contained no undissolved matters.

In addition, during the hydrolyzation and active carbon treatment, oxygen was bubbled to remove the generated ammonia as rapid as possible and to prevent the acrylamide from polymerizing.

The polyacrylamide made from acrylamide which was not subjected to hydrolysis and an active carbon treatment contained a considerable amount of undissolved matters.

EXAMPLE 5

To an aqueous solution containing 30% of acrylamide at a temperature of 40°C which was prepared by a catalytic hydration method was added 1.0% of sodium hydroxide based on the acrylamide and the resulting solution was kept at that temperature under air blowing for 6 hours. The solution so treated was neutralized with sulfuric acid to a pH value of 6.5. An aqueous solution containing 20% of this acrylamide alone was polymerized with the use of a redox initiator to produce polyacrylamide having a molecular weight of about 7,000,000. The resulting polymer was dried at a temperature of 60°C to give powdery polyacrylamide.

The so so-obtained wet polymer and dry polymer were dissolved in water at a concentration of 0.1% and both of them was found to dissolve completely.

When the non-treated acrylamide was polymerized in a similar manner, both wet polymer and dry polymer were proved to contain undissolved matters and in particular, the dry polymer was substantially undissolved.

We claim:

1. A process for purifying an acrylamide containing cross-linking impurities which comprises adding an inorganic base (excluding ammonia) to an aqueous solution containing 15 to 60% by weight of the acrylamide at a temperature of up to 60°C, in a quantity of 0.1 to 1.5% based on the acrylamide; and blowing a gas inert to the acrylamide into the resulting mixture at a hydrogen ion concentration of pH of 12 to 13.7 thereby carrying off, by the gas, ammonia which is a hydrolysis product of said cross-linking impurities from the aqueous solution in which the acrylamide remains substantially intact.

2. The process according to claim 1 wherein air or oxygen is used as the gas inert to the acrylamide.

3. The process according to claim 1 wherein said temperature ranges from 40° to 50°C.

4. The process according to claim 1 wherein the pH is maintained in a range of from 12.8 to 13.5.

5. The process according to claim 1 wherein the inorganic base is a member selected from the group consisting of hydroxides, carbonates, and phosphates of alkali metals and alkaline earth metals.

6. The process according to claim 1 wherein the inorganic base, when it is a caustic alkali, is added in a quantity of 0.1% by weight relative to the acrylamide.

7. The process according to claim 6 wherein particularly 0.2 to 1% by weight of the caustic alkali is used.

8. The process according to claim 1 wherein when a blowing orifice of a diameter of less than 0.1 mm is used, the gas is blown at a superficial velocity in a column of not less than 0.5 mm/second.

9. The process according to claim 8 wherein the gas is blown particularly at a superficial velocity in a column of 2 to 5 mm/sec.

10. The process according to claim 1 wherein when a blowing orifice having a diameter of 2 to 4 mm is used, the gas is blown at a superficial velocity in a column of not less than 3 mm/sec.

11. The process according to claim 10 wherein the gas is blown particularly at a superficial velocity in a column of 7 to 20 mm/sec.

12. The process according to claim 1 wherein the inert gas is blown through a gas diffuser made of a sintered metal or sintered glass.

13. A process for purifying an acrylamide containing cross-linking impurities which comprises adding an inorganic base (excluding ammonia) to an aqueous solution containing 15 to 60% by weight of the acrylamide at a temperature of up to 60°C, in a quantity of 0.1 to 1.5% based on the acrylamide, blowing a gas inert to the acrylamide into the resulting mixture at a hydrogen ion concentration of pH of 12 to 13.7 thereby carrying off by the gas, ammonia which is a hydrolysis product of said cross-linking impurities from the aqueous solution in which the acrylamide remain substantially intact, and subjecting the acrylamide solution, thus treated, to an activated carbon absorption treatment.

14. The process according to claim 13 wherein the activated carbon treatment is carried out simultaneously with or before the blowing of the inert gas.

15. The process according to claim 14 wherein a coconut shell active carbon produced by a steam process is used in the active carbon treatment.

* * * * *